United States Patent
Samain et al.

(10) Patent No.: US 11,647,825 B2
(45) Date of Patent: May 16, 2023

(54) METHOD FOR MANUFACTURING A PERSONALIZED APPLICATOR FOR THE APPLICATION OF A COSMETIC COMPOSITION

(71) Applicant: L'OREAL, Paris (FR)

(72) Inventors: Henri Samain, Chevilly-la-Rue (FR); Jean-Baptiste Blanc, Chevilly-la-Rue (FR); Franck Giron, Chevilly-la-Rue (FR); Chrystele Gevrey, Chevilly-la-Rue (FR); Nadia Gardel, Chevilly-la-Rue (FR)

(73) Assignee: L'OREAL, Paris (FR)

( * ) Notice: Subject to any disclaimer, the term of this patent is extended or adjusted under 35 U.S.C. 154(b) by 274 days.

(21) Appl. No.: 16/757,018

(22) PCT Filed: Oct. 19, 2018

(86) PCT No.: PCT/EP2018/078761
§ 371 (c)(1),
(2) Date: Apr. 17, 2020

(87) PCT Pub. No.: WO2019/077131
PCT Pub. Date: Apr. 25, 2019

(65) Prior Publication Data
US 2020/0337444 A1    Oct. 29, 2020

(30) Foreign Application Priority Data

Oct. 20, 2017 (FR) ........................................ 1759938
Oct. 20, 2017 (FR) ........................................ 1759943

(51) Int. Cl.
*A45D 40/26* (2006.01)
*A45D 44/00* (2006.01)
(Continued)

(52) U.S. Cl.
CPC ........... *A45D 44/005* (2013.01); *A45D 40/26* (2013.01); *A45D 40/30* (2013.01); *B29C 64/10* (2017.08);
(Continued)

(58) Field of Classification Search
CPC ... B29C 64/10; B29C 64/106; B29C 67/0066; B29C 67/0088; B29C 64/171;
(Continued)

(56) References Cited

U.S. PATENT DOCUMENTS 1,556,744 A   10/1925   Ansehl
1,782,911 A   11/1930   Scrimgeour
(Continued)

FOREIGN PATENT DOCUMENTS

EP    1810594 A1    7/2007
EP    2460435 A1    6/2012
(Continued)

OTHER PUBLICATIONS

Patent Translate, "Description FR2980345A1", Jun. 23, 2022, EPO and Google. (Year: 2022).*
(Continued)

*Primary Examiner* — Joseph S Del Sole
*Assistant Examiner* — Margaret B Hayes
(74) *Attorney, Agent, or Firm* — Shumaker, Loop & Kendrick, LLP

(57) ABSTRACT

Method for manufacturing a personalized applicator for applying a product, notably make-up product, to keratinous materials, including a application surface. The method includes the following steps: a) applying to a surface of the keratinous materials of an individual a composition that modifies the appearance thereof, b) performing an optical acquisition of the topography of the surface thus covered and of at least one image providing information as to the
(Continued)

location of the composition, and c) from this acquisition creating the applicator or a mold intended for the manufacture thereof.

31 Claims, 15 Drawing Sheets

(51) Int. Cl.
| | |
|---|---|
| *B33Y 10/00* | (2015.01) |
| *B33Y 50/02* | (2015.01) |
| *B33Y 80/00* | (2015.01) |
| *B29C 64/393* | (2017.01) |
| *B29C 64/10* | (2017.01) |
| *A45D 40/30* | (2006.01) |
| *B29L 31/00* | (2006.01) |

(52) U.S. Cl.
CPC ............ *B29C 64/393* (2017.08); *B33Y 10/00* (2014.12); *B33Y 50/02* (2014.12); *B33Y 80/00* (2014.12); *B29L 2031/718* (2013.01)

(58) Field of Classification Search
CPC ..... B29C 64/176; B29C 64/182; A45D 29/00; A45D 31/00; A45D 29/004
See application file for complete search history.

(56) References Cited

U.S. PATENT DOCUMENTS

| | | | |
|---|---|---|---|
| 1,944,691 | A | 1/1934 | Libby |
| 2,199,720 | A | 5/1940 | Catelin |
| 2,207,959 | A | 7/1940 | Way et al. |
| 2,248,533 | A | 7/1941 | Gibert |
| 2,279,781 | A | 4/1942 | Fogarty |
| 2,412,073 | A | 12/1946 | Bassett |
| 2,416,029 | A | 2/1947 | Turnes |
| 2,554,965 | A | 5/1951 | Steven et al. |
| 2,646,054 | A | 7/1953 | Greene et al. |
| 2,735,435 | A | 2/1956 | Feinstein |
| 3,308,837 | A | 3/1967 | Selleck |
| 6,070,598 | A | 6/2000 | Gueret |
| 9,058,765 | B1 | 6/2015 | Mallick et al. |
| 2003/0209254 | A1 | 11/2003 | Ruggiero |
| 2009/0151741 | A1 | 6/2009 | Ngo |
| 2010/0322693 | A1 | 12/2010 | Mallardi, III |
| 2011/0123703 | A1 | 5/2011 | Mohammadi et al. |
| 2012/0192884 | A1 | 8/2012 | Nasu et al. |
| 2015/0050624 | A1* | 2/2015 | Yamanashi ............ A45D 44/00 434/100 |
| 2015/0055085 | A1* | 2/2015 | Fonte .................... G02C 13/003 700/98 |
| 2016/0000208 | A1 | 1/2016 | Wong |
| 2017/0354806 | A1* | 12/2017 | Stanley .................. A61H 39/02 |
| 2018/0092452 | A1* | 4/2018 | Chun ...................... A45D 34/04 |

FOREIGN PATENT DOCUMENTS

| | | | | |
|---|---|---|---|---|
| FR | 663805 | A | 8/1929 | |
| FR | 752860 | A | 10/1933 | |
| FR | 2915820 | A1 | 11/2008 | |
| FR | 2980343 | A1 | 3/2013 | |
| FR | 2980345 | A1 * | 3/2013 | ......... A45D 40/0087 |
| FR | 2980345 | A1 | 3/2013 | |
| FR | 2984699 | B1 | 6/2013 | |
| FR | 3049832 | A1 | 10/2017 | |
| WO | 2008013608 | A2 | 1/2008 | |
| WO | 2013045332 | A1 | 4/2013 | |
| WO | 2013092726 | A2 | 6/2013 | |
| WO | 2017053489 | A1 | 3/2017 | |

OTHER PUBLICATIONS

International Search Report (ISR) for PCT/EP2018/078761 dated Dec. 12, 2018 (4 pages).
Written Opinion of the International Searching Authority for PCT/EP2018/078761 dated Dec. 12, 2018 (6 pgs.).
International Search Report (ISR) for PCT/EP2018/078756 dated Dec. 13, 2018 (4 pages).
Written Opinion of the International Search Authority for PCT/EP2018/078756 dated Dec. 13, 2018 (4 pages).
Stevie et al. "Fabrication of Personalized Lipstick Applicator Using 3D Printing Technology", The International Federation of Societies of Cosmetic Chemists, Conference 2017 (1 pg.).
("machining." Merriam-Webster Online Dictionary. 2010. Merriam-Webster Online. Feb. 19, 2010 <http://www.merriam-webster.com/dictionary/machining> (Year: 2010.
Non-Final Office Action issued in U.S. Appl. No. 16/757,076 dated Jul. 14, 2022 (26 pages).
Requirement for Unity of Invention for U.S. Appl. No. 16/757,076, mailed Feb. 8, 2022 (8 pages).
Final Rejection issued for U.S. Appl. No. 16/757,076, dated Mar. 3, 2023 (24 pages).

* cited by examiner

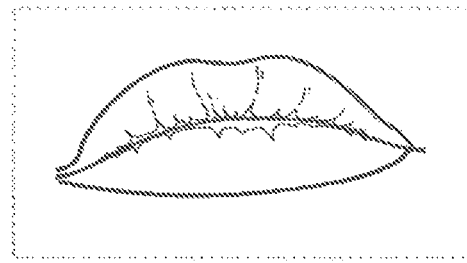 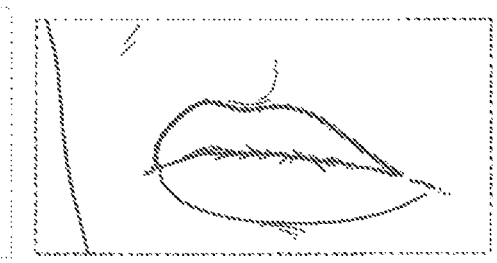
Fig. 5A　　　　Fig. 5B
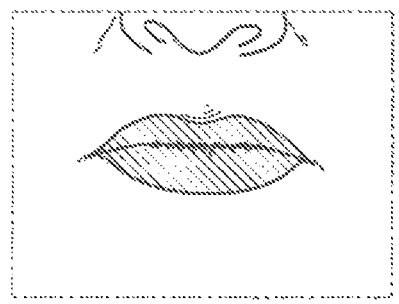 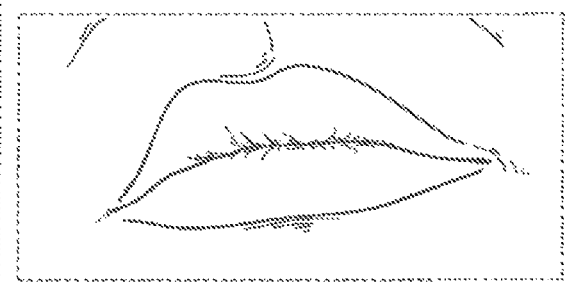
Fig. 6A　　　　Fig. 6B
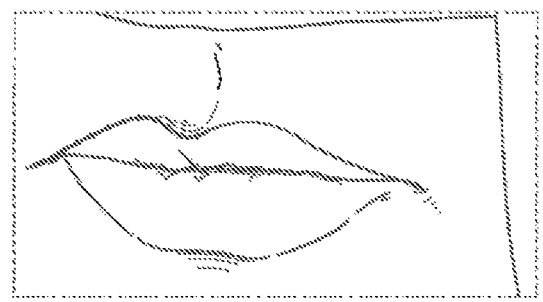
Fig. 6C

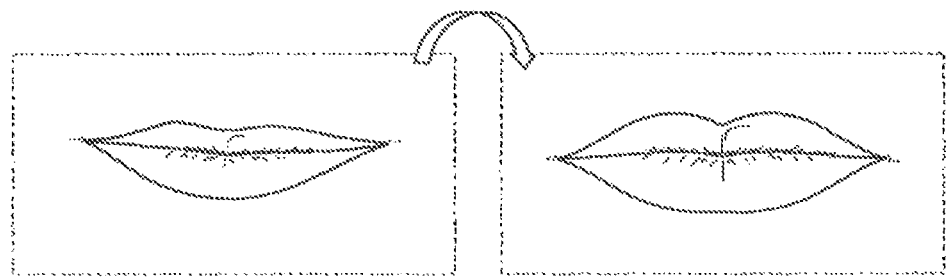
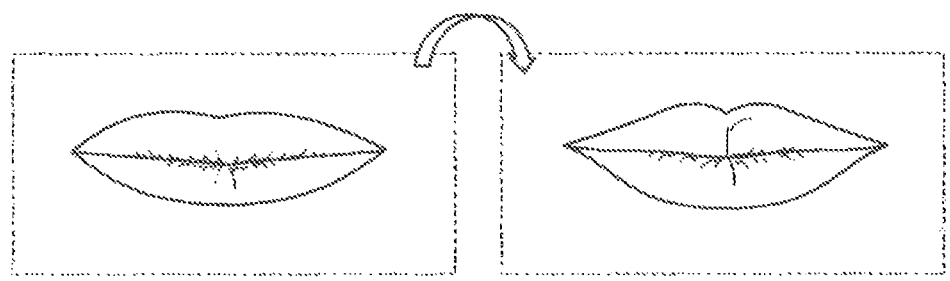
Fig. 22A    Fig. 22B
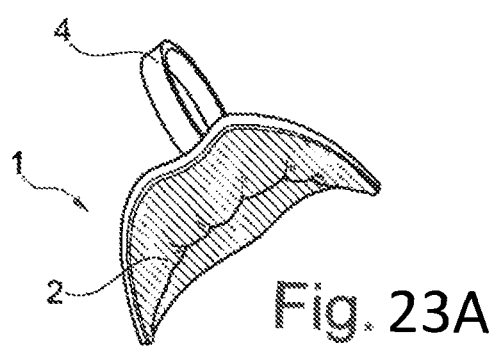
Fig. 23A
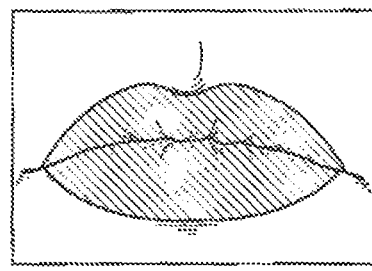
Fig. 23B
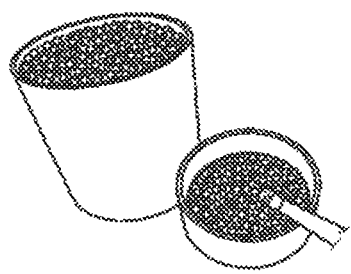
Fig. 23C
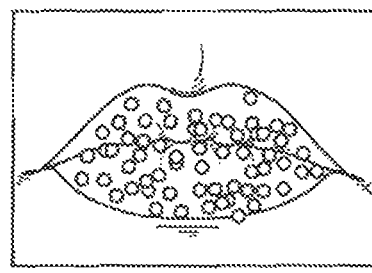
Fig. 23D

METHOD FOR MANUFACTURING A PERSONALIZED APPLICATOR FOR THE APPLICATION OF A COSMETIC COMPOSITION

TECHNICAL FIELD

The present invention relates to the methods for manufacturing a personalized applicator for applying a cosmetic composition to keratinous materials, notably the lips. The invention also relates to the personalized applicators thus manufactured and to the cosmetic treatment methods, notably make-up, that use them.

BACKGROUND

In order to apply make-up to the lips, the usual method is to apply a film of covering and/or coloring composition using an applicator such as a lip brush or a stick of lipstick, which is moved along the lips in order to cover the surface thereof. The user can see the effect obtained but may be unsatisfied with the result. In particular, if she believes that the shape of her lips do not suit her, the user remains disappointed with the result. This is what happens with individuals who, for example, consider their lips to be too thin, too wide, asymmetric or badly proportioned with respect to the shape of their face.

Some individuals consider changing the outline when applying the composition, but it is extremely difficult not to follow the natural outline of the lips. The problem is even greater in individuals who have difficulty with the application, for example those who have eyesight or motor skills problems. The difficulty increases further if the color of the lipstick is particularly pronounced, particularly if it is dark in color, and/or if the product is particularly hard-wearing, for example being a formulation said to be «long-lasting». In attempting to modify the outline, the chances therefore are that the results will be asymmetric, or will extend beyond the natural outline to an exaggerated degree, thus rendering the result unattractive or even ridiculous.

In any case, whether the individual sticks to the natural outline of their lips, or whether they attempt to rectify the outline thereof, the impression of not achieving an attractive result may drive certain individuals to give up applying make-up to their lips. Some do not give up, but take far longer to apply their make-up, attempting to avoid the above problems. Many will need to resort to successive removals and reapplications of make-up. The procedure is therefore lengthy, irritates the mucous membranes and users are driven to applying make-up only occasionally and/or to choosing the most neutral colors possible, thus reducing the benefit of applying lip make-up. The same problems arise in applying make-up to the eyelids or the cheeks.

Users generally desire a clean lip make-up look, yet at the same time prefer to use a stick of lipstick. Unfortunately, the latter is ill suited to the creation of clean error-free outlines, and the use of a pencil is not always easy especially when not wishing to follow the natural outline of the lips.

Documents FR 752 860, U.S. Pat. Nos. 2,279,781, 2,207, 959, FR 663 805, U.S. Pat. Nos. 2,412,073, 3,308,837, 2,735,435, 1,556,744, 2,248,533, 2,416,029, 1,944,691, 1,782,911, 2,554,965, 2,199,720, WO 2008/013608, US 2003/209254 and US 2010/0322693 describe how to produce an applicator the application surface of which has the predetermined shape of a mouth. This solution makes it possible to create a standard make-up look but is somewhat unsatisfactory because it does not always conform to the three-dimensional morphology of the lips and therefore leaves regions uncovered.

One trick may be to pinch the lips together in order to spread product between regions in which it is present and other regions in which it is less so, but this action has a tendency to alter the outlines. The risk then is that once again the product does not follow the Cupid's bow, giving an unsatisfactory appearance. The corners of the lips and the Cupid's bow are in fact the hardest regions of the lips to which to apply make-up and to outline. One possibility is to ask a third party, for example a make-up professional, also referred to as a «make-up artist», to create the outline, using a product that leaves a lasting mark, such as tattooing for example. However, in practice, the operation is not readily acceptable because most users do not wish to wear their lip make-up all of the time.

Application US 2012/192884 describes a method for manufacturing a face treatment mask intended to be fixed on the face of an individual so as to cover their face, having an interior surface of a shape that conforms to the shape of the face of the individual. The method uses data taken from three-dimensional images of the individual's face.

Application US 2011/123703 relates to a method for the targeted and personalized distribution of a user's skin care agents. The image of a predetermined treatment zone of the skin is captured by an imaging device, and from this a skin profile unique to the user is generated. On the basis of this profile, one or more sheets intended to be applied to the predetermined treatment zone is or are printed. Each of the sheets comprises a substrate with several isolated distinct regions, at least two of these regions being printed with different skin care agents chosen according to the user's skin profile.

Application US 2009/151741 describes a method for creating a personalized cosmetics stencil, using a transfer support placed on a region of the face to which cosmetic products are applied. An image is generated from an impression of the region placed on the transfer support, and a stencil is obtained by forming an opening in a template support corresponding to the image, making it possible to reproduce the desired make-up effect.

Application US 2016/000208 describes a make-up applicator for foundation, comprising a complete 3D mask of the face, an adhesive layer and a layer of composition for transferring the product.

The article by M. Stevic et al. "*Fabrication of personalized lipstick applicator using 3D printing technology*", published in "The International Federation of Societies of Cosmetic Chemists" conference, 2017, describes how to obtain a personalized block of lipstick from a mold created by 3D printing following acquisition of the profile of a user's lips using a 3D scan. The chief disadvantage with this method is that the applicator has a tendency to lose its shape with repeated applications to the lips, to the detriment of the precision of the make-up application. In addition, it is awkward to achieve transfer from a block of product without a shearing movement obtained by moving the block over the skin.

Other solutions have been described in applications WO 2013/045332, FR 2 980 345, WO 2013/092726, and FR 2 984 699 for producing an applicator suited to the individual morphology of the lips. In order to achieve this, an impression of the user's lips is produced from a record of the outline of the lips corrected generically, and then a countermold is produced which will be used as an applicator. The user places the product in the countermold, before applying to her lips. Another option is to deliver the product through the countermold, via a multitude of holes. This solution constitutes progress, particularly as regards the cleanness and speed of application, but does not allow ideal make-up application.

Neither do these solutions allow the applicator to be made available to the user very quickly. Being able to make the applicators available quickly is important because that allows the user to be able to check the result by conducting one or more tests, particularly in the case of a desired change to the shape of her made-up lips, but also in the case of individuals with visual or motor-skills problems or a lack of experience. This need is also driven by instances in which the user wishes to make multiple small steps toward the solution that will best suit her. It may be advantageous to have several applicators, for example in instances in which the user has a number of different ideas about the outline and wishes to try out several results.

The possibility of requesting and quickly obtaining a new applicator is also attractive. Indeed, when traveling, an individual will sometimes forget to bring some of their make-up. As a result, an individual wishing to present herself with her customary look will find herself in a tricky situation because she will have to choose between not applying make-up, or applying make-up using a product available at a sales outlet near where she is. In the latter case, she may not have access to a personalized applicator and will have to fall back on conventional products such as sticks of lipstick or brush applicators, with the risk of being less successful in achieving her make-up look.

Moreover, a person may lose or damage their applicator.

Users may also wish to swap applicators with one another or demonstrate their applicator, even though the shape is personalized, in a desire to give or ask advice, particularly of friends or of a make-up artist. If the individual with whom one wishes to share one's applicator is not nearby, the only option at the present time is to take a photograph of the result after application and send it to that individual. The rendition is then approximate and the advice somewhat irrelevant. It would therefore be beneficial to be able to show the actual object.

Objective of the Invention

There is therefore a need to create, in a short space of time, an applicator that is personalized to the desired shape, that yields a faithful and harmonious make-up look according to the user's face, notably following the ideal outline of the lips.

SUMMARY OF THE INVENTION

The invention notably seeks to meet this objective and its subject, in one of its aspects, is a method for manufacturing a personalized applicator for applying a product, notably make-up product, to keratinous materials, notably the lips, comprising an application surface, the method comprising the following steps:

a) applying to a surface of the keratinous materials of an individual a composition that modifies the appearance thereof, b) performing an optical acquisition of the topography of the surface thus covered and of at least one image providing information as to the location of the composition, and c) from this acquisition creating the applicator or a mold intended for the manufacture thereof.

The topography may be obtained by a 3D scan of the surface covered with composition, notably by projecting structured light onto said surface or by performing a photogrammetric acquisition. The image providing information as to the location of the composition may be a photograph of the mouth of the individual, for example taken using the same device as the one used for the acquisition of the topography.

According to another of its aspects, a subject of the invention is a method for manufacturing a personalized applicator for applying a cosmetic composition to the lips, this applicator comprising an application surface made from a material that can become laden with composition, the method comprising the following steps:

a) performing a 3D scan of the topography of at least part of the surface of the lips, and b) from at least said scan, creating at least part of the applicator or a mold used for the manufacture thereof, by machining a preform or by additive manufacturing.

The scan of the topography of the lips may include the scan of a region of skin extending around the mouth, and preferably excludes the scan of other regions of the face, such as the nose, the cheeks, the eyes or the forehead.

The invention makes it possible to achieve a professional-quality make-up look oneself, on a surface of the keratinous materials, preferably the lips, but equally the eyelids or any other region of the face, for example the cheekbones, thanks to a morphological applicator tailor-made to suit the user.

The personalized applicator according to the invention in particular makes it possible to define the mouth perfectly, and to color it evenly, if desired.

Acquisition and Reworked Surface

The outline of the application surface of the applicator may correspond to the natural outline of the lips.

In an alternative, the outline of the application surface diverges from the natural outline of the lips in order, for example, to correct a defect or to change the appearance of the made up lips.

Either one of the aforementioned methods may involve creating an outline which differs from the natural outline of the scanned lips, notably a different shape of Cupid's bow and/or a different height and/or a different width. It is thus possible to define the outline that best suits the user, having a shape considered to be ideal, for example using a lip pencil. This outline may be created during the application of the aforementioned composition and/or using software.

Either one of the methods may thus comprise a step involving generating a reworked 3D surface from the data derived from the acquisition of the topography of the surface, notably using image processing software.

What is meant by a «reworked 3D surface», is a surface the shape and/or outline of which has been modified by comparison with the natural surface the topography of which was acquired.

Either one of the methods may comprise the generation of a reworked 3D surface different than the natural surface of the lips, the applicator or the mold used for its manufacture having a shape given at least in part by this reworked surface.

The invention makes it possible to offer a make-up result with a clean outline, improving the harmony of the face. The invention also offers a way of applying make-up very quickly, in a single gesture, and anywhere, even without a mirror, for example in the car or at the office.

The invention allows make-up to be applied in bright colors and/or using a long-lasting composition without risk, even on a daily basis because the personalized applicator makes it possible to avoid the failures that occur when this type of product is applied using known applicators.

The personalized applicator according to the invention makes it possible to redefine the outline of the lips, providing a remodeling effect, and can therefore be used by individuals whose outline has become indefinite, notably as a result of the ageing of skin, and who no longer dare to apply make-up.

The invention also offers the possibility of applying lip make-up in the style of somebody else, for example a star with an iconic smile.

The reworked surface may potentially diverge from the natural surface of the lips inside the outline thereof, in the order to leave a space between the application surface and the scanned lips when the applicator is applied to the lips in the normal way. This space may serve to accommodate a self-expanding composition as will be detailed later on.

The reworked surface may coincide with the natural surface of the lips resulting from the scan, except for its outline which differs from the natural outline of the scanned lips, in order to modify the outline of the made up lips.

In order to perform the 3D scan it is possible to use any 3D scanner capable of capturing the volume and the dimensions of the zone concerned. For preference, use is made of a 3D scanner able also to capture the color and appearance of the zone concerned, so as to acquire one or more images providing information as to the location of the composition.

The 3D scan is advantageously a scan produced by projecting fringes of light, but any other structured light is possible.

Either one of the methods according to the invention may comprise a step involving giving the user the option to choose between at least two make-up results, the reworked surface being generated at least on the basis of this choice, for example automatically using software.

Either one of the methods may comprise a step involving allowing a user to model a surface obtained from the 3D scan, notably the outline thereof, and thus generate the reworked surface. The modelling may be performed remotely using software from a workstation to which the data representative of the 3D scan have been transmitted over a telecommunications network, notably over the Internet or by GSM/GPRS. This remote workstation is, for example, that of a make-up artist.

Thus, either one of the methods may involve establishing a remote connection to a third party providing a model to propose to the individual whose lips have been scanned according to the physiognomy of this individual, for example using an Internet based video-telephony platform.

Either one of the methods may involve detecting, notably automatically using software, asymmetry of the lips and/or the face; the calculation of the reworked surface may be performed, preferably automatically, at least with consideration to the detected asymmetry.

Either one of the methods may involve outlining, preferably automatically, the lips from at least one image thereof. A curve derived from the outlining, and known as a «spline», may be created, notably having at least 10 control points, and better, at least 20 control points. If appropriate, an operator is allowed to modify the location of these control points, for example by working on an on-screen depiction of the lips.

Either one of the methods may involve determining a plurality of points on the natural outline of the lips, notably from at least one image thereof, and estimating the natural outline of the lips by interpolation between these points.

Either one of the methods may involve determining a plurality of points on the outline of the reworked surface, notably from at least one image allowing an operator visually to position points through which he wishes the outline to pass, and generating at least part of the outline of the reworked surface by interpolation between these points.

Either one of the methods may involve displaying the natural surface of the scanned lips and/or a make-up result obtained with the applicator and/or the reworked surface.

Either one of the methods may involve displaying at least a portion of the face of the individual with a simulation of the keratinous substance make-up, notably the lip make-up, such as can be obtained with the personalized applicator. Thus, the individual for whom the applicator is intended may monitor the progress of the operations, thus allowing her to satisfy herself of the correct result as early on as possible and, if necessary, ask to make corrections.

Prior Application of a Composition

The 3D scan may advantageously be preceded, as mentioned hereinabove, by the application to the lips of the composition according to a defined outline. This outline may correspond to the natural outline of the lips, notably when there is no wish to modify this with the make-up. In an alternative, this outline corresponds to that of the application surface that is to be created, which differs from the natural outline of the lips.

The surface to which the composition is applied may extend over at least part of the lips and/or over at least part of the skin around the lips, notably when it is a matter of correcting the natural outline of the lips.

The composition is preferably applied in such a way as to redefine the outline of the lips.

The composition may overspill onto the skin at least at one point. As an alternative or in addition, the composition is applied to at least one place that is set back from the natural outline of the lips. The composition may be applied in such a way as to redefine the Cupid's bow and/or as to modify the height of the lips, the width of the lips and/or correct a symmetry.

The composition may be a lipstick, notably a white lipstick. Such a color may make it easier to acquire the topography and/or to visualize the outline of the composition, notably for the purposes of automatic outlining. The composition is preferably of a color that exhibits a pronounced contrast with the rest of the face, so that the outline of the region to which the composition has been applied can be captured easily. The composition preferably has good enough coverage that the natural outline of the lips does not show through it.

The composition is preferably of a matte appearance, thereby reducing the incidence of unwanted reflections. In an alternative in which a composition with a gloss appearance is used, optical means such as polarizers may be used during acquisition in order to reduce brightness. In yet another alternative form, the lips are covered with a fine coat of a mattifying product, such as talc.

The composition may be applied in a uniform coat. In an alternative, the composition is applied along a line delimiting a zone, notably the outline of the lips.

The composition may be applied in sufficient thickness that the border created on the lips is detectable during the acquisition of the topography, notably in the case of the use of a 3D scanner incapable of detecting color. A composition capable of being applied in sufficient thickness, such as a silicone paste, may be used. An adhesive filament may also be applied along the outline of the make-up look that is to be achieved.

Either one of the methods may involve displaying on a screen at least one model of an application, and potentially selecting a model, the composition being applied according to this model.

For preference, a make-up artist is present to advise the user, for example at a sales outlet or in an institute. The make-up artist advantageously applies the composition to the user's keratinous materials according to her expertise and to suit the face as a whole.

The ideal shape may be dependent on the desired color of the make-up. In order to avoid a high number of applications and removals of make-up, when looking for the ideal shape in different colors of make-up, one or more photographs may be taken of one or more different examples of make-up in a given color and then image retouching software can be used to alter the color in order to check that the result is still compatible. If not, the process is started over. The ideal shape may also be dependent on the desired finish for the make-up, the skill of the individual, their hairstyle, and the lighting in the room. The search may thus be conducted, in the same way, for different desired make-up conditions, different skill levels, different hairstyles, and/or different room lightings, in actual conditions or by successive simulations using image retouching software.

It is also possible to use a first composition to look for the ideal outline, and then use a second composition more suited to zone topography acquisition, because it behaves better with respect to the structured light used during topography acquisition, or because it is easier to apply in sufficient thickness, as described hereinabove. An adhesive filament may be used to trace the outline of the region covered with the first composition and then the topography acquisition is performed using the filament once the make-up has been removed from the lips. The results obtained with the first composition may be stored by taking a photograph.

Various tests seeking the ideal shape may be conducted by different make-up artists each having their own experience. One artist may make use of the work done by a predecessor while at the same time looking for possible improvements.

The user may also herself apply make-up she deems to be ideal and then turn to an operator for the topography acquisition aspect. Thus, the topography acquisition step may be performed at a later date and at a location other than that at which the ideal shape was researched.

Either one of the methods may involve establishing a remote connection with a third party who guides the individual through the application of the composition. In an alternative, an electronic assistant guides the user, notably on a computer or smart phone.

The keratinous materials, notably the lips, may be made up according to a result validated by the individual, and then have the make-up removed, a composition more suited to topography acquisition then being applied to the same outline as the one just validated, so that the 3D scan can be done.

The make-up result obtained after application of the composition is advantageously validated by the individual before proceeding with the optical acquisition of the topography of the surface.

Either one of the methods may involve automatically outlining the region covered with composition by using image processing. A visual check may then be made to ensure that this outlining is correct.

Either one of the methods may involve manually identifying points in the image of the region covered with composition and automatically determining, from these points, an outline used to create the applicator or the mold.

Applicator Manufacture

A file that can be read by a CNC machine (Computer Numerical Control machine) or a 3D printer is advantageously generated and can be stored, notably automatically, for example in the cloud or on a central server, and sent to all user access points, for example sales outlets or institutes. The file may be sent to the user. It is also possible to keep files not adopted, in order to avoid redundant testing.

A translated numerical copy of a surface, possibly a reworked surface, obtained from the 3D scan of the lips, is advantageously created, and then a smoothed volume of the applicator or of the mold between said surface and the translated copy thereof may be generated. In an alternative, a smoothed volume of the applicator or of the mold is generated between said surface and a standard applicator surface, notably one created by learning from several acquired surfaces.

In a variant, to obtain a volume, a shell function may be used, as the one provided by the Geomagic Wrap 3D toolbox. Such a function creates, from a surface, a volume of constant thickness according to each local norm. In this case, the outer surface of the applicator is thus no longer a copy of the functional surface but a mathematical generation of the shell function.

The applicator is preferably produced with a handle on the back. Said handle may be removable or may attach with a clip.

One or more distinctive signs, such as a make and/or a forename, may be inscribed on the applicator, for example so as to be able to recognise the make and/or the owner.

The applicator may be produced by machining, preferably by micro-machining. Advantageously, a preform chosen, notably automatically, from among many according to the shape that is to be obtained after machining, is machined. This makes it possible to shorten the manufacturing time. These preforms may have been made to measure, for example from various mouths, and their face that is to be machined is advantageously larger than the surface area of the natural lips. The preforms may have a verso face already formed, with or without handle, or with or without a system for attaching a handle to it, or with or without a system to which to attach a compartment capable of containing a cosmetic product.

The chosen preform may correspond to a countermold produced from an impression of the user's lips. This impression may be made using a curable material. The user's lips are advantageously kept still and closed during application of the curable material, until the material has at least partially solidified.

The edges and the upper surface of the preform, which correspond to the application surface of the applicator, are advantageously machined, for example mechanically, by laser, waterjet, or grinding wheel, according to the desired outline determined by the reworked 3D surface. As this shaping process takes just a few minutes, it becomes possible to purchase the applicator at the sales outlet and leave without having to wait. It is thus possible to offer the user several different applicators, that the user can test for comparison and select the one or those he or she prefers.

If the applicator is produced with a handle, a preform that already comprises the handle is advantageously machined. In an alternative, the preform is machined in such a way as to be able to accept a removable handle or handle that can be clipped on.

The invention offers, if so desired, the option of reproducing the applicator remotely, either when traveling having forgotten to bring it, or because it has been lost, or because someone wishes to share their applicator with somebody else. All that is required is to send the 3D file stored in a computer memory, or have it sent, so that a reproduction thereof can be made anywhere.

In an alternative, the applicator or a mold intended for its manufacture, is produced by an additive method, notably by 3D printing, possibly from a preform.

The 3D printer may be a filament printer. The 3D printer used may achieve a precision in Z of 0.5 mm, better 0.1 mm, better still 0.03 mm.

In the case of 3D printing, the printing can be done onto a support or predetermined objects such as, for example, a preform with or without a handle, with or without a system for attaching a handle to it, or with or without a compartment capable of containing a cosmetic product.

For preference, the applicator becomes laden with composition, completely or partially, by being brought into contact with a pad soaked in composition. The pad is advantageously domed on its surface intended to come into contact with the application surface, so as to adapt to the shape of the applicator. In alternative forms, the applicator is laden with composition directly by means of a block of composition, alternatively of a flocked applicator, of a brush or any other application means impregnated with composition.

As an alternative, the applicator is designed to deliver the cosmetic composition intended to be applied to the keratinous materials, and may comprise a reservoir attached on its back. In an alternative, the applicator is mounted on a reservoir at a later time.

The application surface of the applicator may be at least partially covered in a flock.

The application surface of the applicator may be configured to apply the composition to all or almost all of the lips, in a single gesture, by pressing the applicator against the lips without a shearing movement.

The applicator may be made from a material having a Shore A hardness greater than or equal to 30 Shore A, or, better, greater than or equal to 60 Shore A.

The applicator may be made from a material having a Brinell hardness below 600 HB, or, better, below 150 HB.

Sequence of Manufacturing Steps

It is possible to combine, in a single location, the operations of defining the outline, acquiring the topography before or after application of the composition, creation of the application surface and manufacture of the personalized applicator.

In that case, manufacture by micro-machining is particularly well-suited because the manufacturing is thus carried out in a very short space of time and with very little handling. As a result, not only is the user not made to wait, but what is more, the risk of confusion when there are several users to be served at the same time is avoided. In an alternative, the operations are performed at several locations, without the user having to travel. For example, the 3D scanning step can be performed where the user is. The step of defining the ideal outline can be performed remotely, somewhere there is a make-up artist to provide assistance in esthetic choice. In that case, the make-up artist receives the file of the scan and can offer the user a number of choices through on-screen modeling sent electronically. That offers interactive advice making it possible to find the best shape of applicator.

The reworked surface may be created remotely, from the file received after defining the ideal shape, the file containing the information about the reworked surface being able to be sent to wherever the manufacturing machine is situated.

Manufacture may be performed remotely, in yet another location, an operator sending the personalized applicator to the user, either at the location at which the first step was performed or to another address, for example directly to the user's home address.

It is also possible to perform several applicator manufacturing operations, for example one manufacture immediately after the 3D scan or the optical acquisition, particularly at the location or close to the location where the user is, and at the same time or subsequently, one or more other manufactures in order to provide the availability of spares. The first manufacture is preferably performed by micro-machining, for example by a low-precision machine. The second manufacture(s) may be performed by micro-machining or by a 3D printer, particularly at a high production rate. The first version of the applicator may be made from a basic-quality material, for example a plastic. The first version of the applicator may be intended to be used for testing, just for a few days, and then abandoned in favor of the later version(s). The later version(s) may be made from a higher-quality material, such as a stronger plastic, a metal or a ceramic.

It is also possible to perform certain operations autonomously.

A user who has already created various personalized applicators according to the invention may create a mean or another combination of the various 3D files recorded during various visits in order to create a new applicator.

Lip Outlining Applicator

In an alternative, the application surface of the personalized applicator is configured to apply the composition to just a portion of the lips, which may correspond to the outline of the lips.

The application surface may reproduce the Cupid's bow of the lips, or even the entire outline of the lips. In that case, the application surface may be at least partially defined by a filamentary or hollowed part of the applicator.

In an alternative form, the application surface is solid, the peripheral part of the application surface, intended for applying make-up to the outline of the lips, being made from a material capable of being laden with composition and different than the material used for creating the rest of the application surface. Only the material of the peripheral part advantageously offers enough adhesion to pick up the product by tamping.

In an alternative, the application surface, with the exception of the peripheral part thereof, is for example coated in flock. In yet another alternative form, a silicone is deposited inside the application surface, with the exception of the peripheral part thereof.

Another subject of the invention, according to another of its aspects, is an applicator for applying, by transfer, a cosmetic composition to the lips, comprising an application surface to be pressed against the lips, configured to apply composition only to the periphery of said lips so as to make-up their outline only.

The application surface may be at least partially defined by a filamentary or hollowed part of the applicator.

In instances in which the application surface is defined by a filamentary part of the applicator, the latter may comprise a central part, which may be extended by a handle on the back, and four arms extending from said central part and at their ends and in their middle supporting the two, upper and lower, parts of the applicator that form the outline of the upper and lower lips respectively. The upper and lower parts advantageously meet at their ends.

In an alternative form, the application surface is solid, the peripheral part of the application surface, intended for applying make-up to the outline of the lips, being made from a material capable of being laden with composition and different than the material used for creating the rest of the application surface.

In an alternative, the application surface, with the exception of the peripheral part thereof, is coated in flock. In yet another alternative form, a silicone is deposited inside the application surface, with the exception of the peripheral part thereof. The flock and the silicone thus load the inside of the lips less than the outline.

The shape of the application surface is advantageously being created from a 3D scan of the lips of an individual. The application surface may reproduce the Cupid's bow of the lips, or even the entire outline of the lips.

The applicator may be configured for simultaneous application of the composition to the upper and lower lips.

According to yet another of its aspects, one subject of the invention is a method for manufacturing an applicator for applying, by transfer, a cosmetic composition to the lips, comprising an application surface to be pressed against the lips, configured to apply composition only to the periphery of said lips so as to make-up their outline only, and comprising the following steps:

a) performing an optical acquisition comprising a 3D scan and the acquisition of at least one image of at least part of the surface of the lips of an individual, and b) from at least said optical acquisition, creating at least part of the applicator comprising the application surface or a mold used for the manufacture thereof, by machining a preform or by additive manufacturing.

The outline of the application surface may correspond to the natural outline of the lips. In an alternative, the outline of the application surface diverges from the natural outline of the lips.

The method may involve creating a reworked outline which differs from the natural outline of the scanned lips, notably a different shape of Cupid's bow and/or a different height and/or a different width.

The method may involve a step consisting in giving a user the option to choose between at least two lip outline make-up results, a surface with a reworked outline being generated at least on the basis of this choice.

The method may involve displaying the natural surface of the scanned lips and/or a make-up result obtained with the applicator and/or the surface with the reworked outline.

The method may comprise the step involving allowing an operator to model a surface obtained from the 3D scan, and of thus generating the surface with the reworked outline. The modeling may be performed from a workstation to which the data representative of the 3D scan have been transmitted over a telecommunications network, notably over the Internet or by GSM/GPRS.

The method may comprise detecting asymmetry of the lips and/or the face and calculating the surface with the reworked outline at least with consideration to the detected asymmetry.

The method may involve an outlining, preferably automatic, of the lips from said at least one acquired image thereof.

The method may involve determining a plurality of points on the natural outline of the lips, notably from said at least one acquired image thereof, and estimating the natural outline of the lips by interpolation between these points.

The method may involve determining a plurality of points on the reworked outline, notably from at least one image allowing an operator visually to position these points, and generating at least part of the reworked outline by interpolation between these points.

A translated numerical copy of a surface obtained from the 3D scan of the lips may be created, and then a smoothed volume of the applicator or of the mold between said surface and the translated copy thereof may be generated.

The applicator may be produced with a handle on the back.

The applicator may be produced by machining. In that case, a preform chosen, notably automatically, from among many according to the shape that is to be obtained after machining, may be machined.

It is possible to machine a preform that already comprises the handle.

In an alternative, the applicator or the mold intended for its manufacture is produced by an additive method, notably by 3D printing.

The method may involve displaying at least a portion of the face of the individual with a simulation of the lip outline make-up such as can be obtained with the applicator.

The 3D scan may be preceded by the application to the lips of a composition according to a defined outline. This outline may correspond to the natural outline of the lips. In an alternative, this outline corresponds to that of the application surface that is to be created.

Method for Cosmetically Treating the Lips

A further subject of the invention is a method for cosmetically treating the lips, notably applying make-up thereto, involving the application of a cosmetic composition to the lips using a personalized applicator for applying a cosmetic composition to the lips, obtained using one or other of the methods defined hereinabove.

The applicator preferably becomes laden with composition by being brought into contact with a pad soaked in composition.

The composition may be self-expanding and may, as it expands, fill the space left between the application surface and the lips, when the applicator is applied to the lips in the normal way. That makes it possible to obtain clean outlines since the product, as it develops, is contained and cannot overspill.

In an alternative, the applicator is heated and laden with composition by being brought into contact with a compact of composition, notably made of wax. That makes it possible to use wax-based lip colors rather than liquid products. On first use, the applicator serves to mold the impression of the lips into the compact, thereby shaping the composition compact to the shape of the lips, and is used thereafter to pick up a layer of lipstick that has been rendered liquid.

In yet another alternative form, the composition is adhesive, the method further comprising the application to the adhesive composition applied to the lips of a second cosmetic composition, notably in powder form.

The composition may be transparent. The applicator makes it easier to apply such a composition to the desired points, in spite of the fact that it is not very visible on account of its transparency.

Method for Applying Make-Up to Outline the Lips

Yet another subject of the invention is a method for applying make-up to the lips, in which method the outline of the lips is defined using an applicator, as defined hereinabove, comprising an application surface to be pressed against the lips, configured to apply the composition only at their periphery so as to apply make-up to their outline only, by loading the application surface with composition and pressing it against the lips.

Such an applicator may or may not be personalized. It allows the lips to be outlined with make-up quickly and accurately in a single gesture by pressing the applicator against the lips.

The applicator may be loaded with composition by bringing it into contact with a pad soaked in composition, notably made of foam.

The applicator may be heated and loaded with composition by being brought into contact with a composition compact.

The space inside the outline may be filled with a liquid, pasty or solid cosmetic composition. The cosmetic composition may be the same color as the drawn outline. The cosmetic composition may be applied by moving a block of product over the lips. In an alternative form, the liquid cosmetic composition is applied with an applicator of the brush or flocked type, or by using a tube with an angled end, or an applicator comprising a ball for application. In yet another alternative form, the cosmetic composition is pasty, notably being contained in a pallet, and may be applied with a brush or with a finger.

In an alternative form, the composition applied inside the outline is different in color from the outline and applied by transfer.

The application surface used to define the outline has preferably been obtained from a 3D scan of the lips of the individual. Likewise, the surface used for applying the composition by transfer inside the contour has preferably been obtained from a 3D scan of the lips of the individual.

If appropriate, an applicator part comprising an application surface configured to apply the composition only to the periphery of the lips so as to outline them in make-up only, and an insert that has a surface used to apply composition by transfer inside the outline and which has been obtained from a 3D scan of the lips of the individual can be fitted together. The applicator obtained can then be pressed onto the lips. The insert may be laden with a different composition than the applicator part used for doing the outline. That makes it easier to achieve a two-product make-up application.

Method for Applying Make-Up to the Keratinous Materials

Another subject of the invention is a method for applying make-up using a personalized applicator for applying a make-up product to the keratinous materials, which is obtained by implementation of the method as defined hereinabove, involving bringing the applicator into contact with the keratinous materials of said individual and transferring a make-up product onto said materials.

The make-up method can be implemented for applying make-up to the lips, said keratinous materials comprising at least part of the lips and, better, of an adjacent area of skin.

Brief Description of the Drawings

The invention will be better understood from reading the following detailed description of nonlimiting embodiments thereof and from studying the attached drawing, in which:

FIGS. 5A and 5B illustrate examples of the acquisition of the topography of the surface of the lips after application of a composition, FIGS. 6A, 6B, and 6C illustrate an examples of the acquisition of the topography of the surface of the lips after application of a composition, FIGS. 22A and 22B depict photographs of lip make-ups achieved with and without an applicator according to the invention, FIGS. 23A, 23B, 23C, and 24D illustrates a lip make-up achieved with an appliciaton according to the invention and an adhesive composition, FIGS. 24A, 24B, 24C, and 24D illustrate a lip make-up achieved with an applicator according to the invention and an adhesive composition.

DETAILED DESCRIPTION

Figure 1:
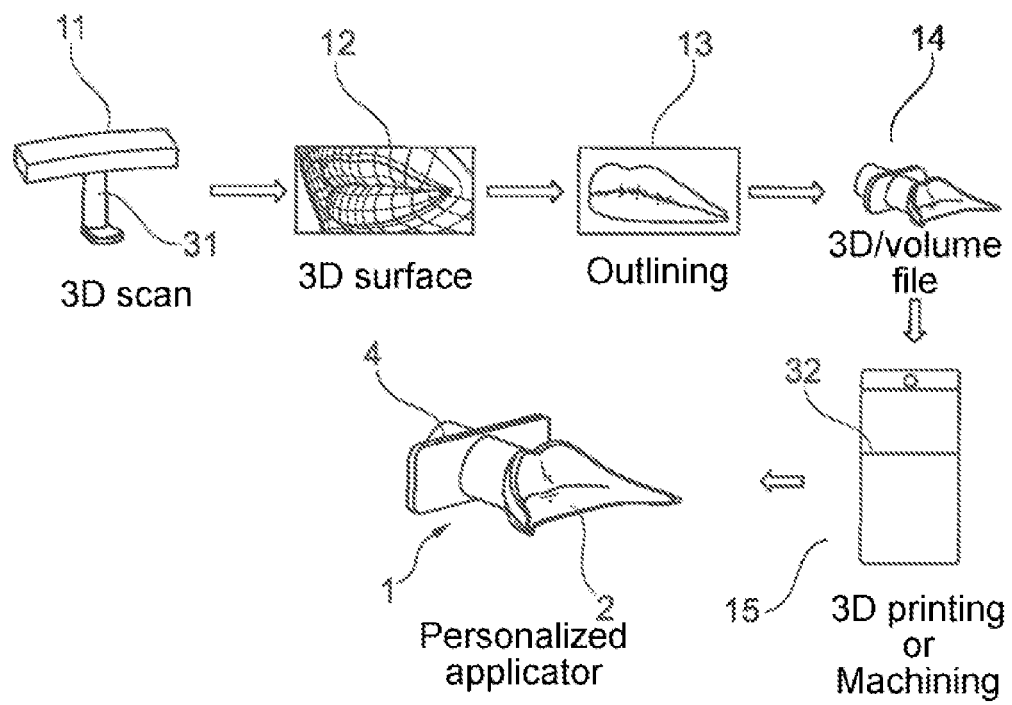
FIG. 1 is an illustration of various steps of an example of a method for manufacturing a personalized applicator according to the invention.

Various steps in an example of a method, according to the invention, for manufacturing a personalized applicator 1 for applying a cosmetic composition to the lips are depicted in FIG. 1 and will be described in detail in what follows.

During a step 11, a 3D scan of the topography of at least part of the surface of the lips of the user is taken using a 3D scanner 31, for example an Artec 3D "Spider" color scanner. Prior to this step 11, a composition may have been applied to at least part of the user's lips, as detailed later on. The 3D scan may include the lips and at least part of the skin around the lips.

During a step 12, a 3D surface is generated from the scan obtained in step 11, for example using 3D software of the Geomagic's Wrap type, and recorded in a file that can be read by a CNC machine, notably a micro-machining machine 35 or by a 3D printer 32. The file is advantageously stored in memory and may be sent to all the user access points, for example sales outlets or institutes, and sent to the user.

The 3D surface generated can be reworked and may be different than the natural surface of the lips.

An outlining, preferably automatic, of the lips on the basis of at least one image thereof may be performed in a step 13.

Figures 9A, 9B:
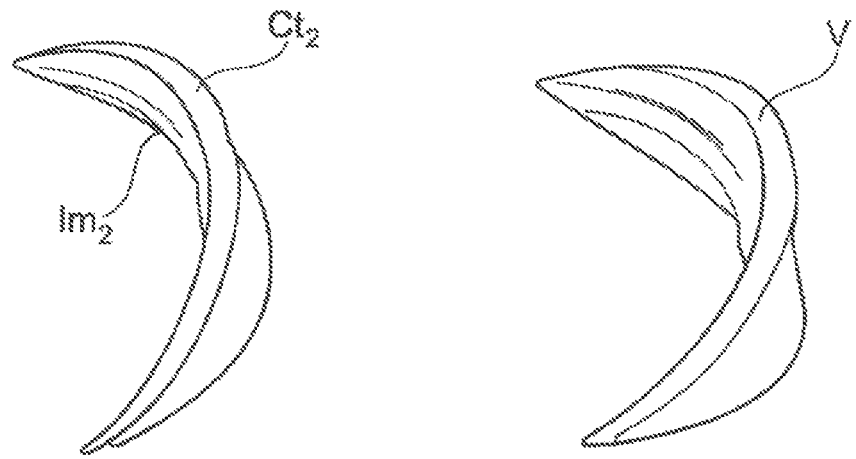
FIGS. 9A and 9B illustrate the creation of a smoothed volume for the applicator using the surface of FIG. 8.

During a step 14, a translated numerical copy $Ct_2$ of the surface $Im_2$ obtained from the 3D scan of the lips is created, and then a smoothed volume V of the applicator or of the mold used for its manufacture between said surface $Im_2$ and the translated copy $Ct_2$ thereof is generated, as depicted in FIGS. 9(a) and (b).

During a step 15, the personalized applicator is produced by 3D printing or by machining from the file of the 3D surface.

In order to create an applicator that makes it possible to achieve make-up perfectly suited to the face shape of the user, an outline which differs from the natural outline of the scanned lips may be generated.

Figure 2:
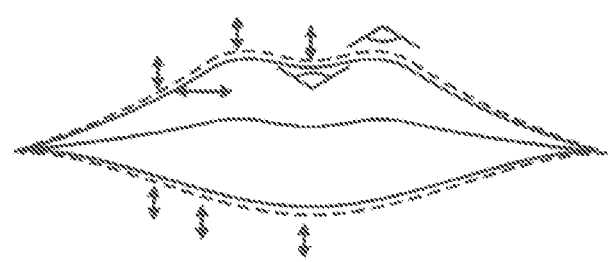
FIG. 2 illustrates parameters that can be modified during the definition of a reworked outline of the lips according to the invention.

The outline of the application surface 2 of the applicator 1 may thus diverge from the natural outline of the lips. As visible in FIG. 2, numerous parameters may be modified when defining the reworked outline of the lips, for example the shape of the Cupid's bow and/or a different height for one and/or other of the upper and lower lips, and/or a different width. An asymmetry of the lips and/or the face may be detected, the reworked outline advantageously taking this into consideration, for example in order to re-establish the appearance of symmetry in the made up lips.

In order to assist with defining the ideal outline and be able more easily to capture the outline of the relevant region, a composition that modifies their appearance may be applied to at least part of the user's lips.

Figure 3:
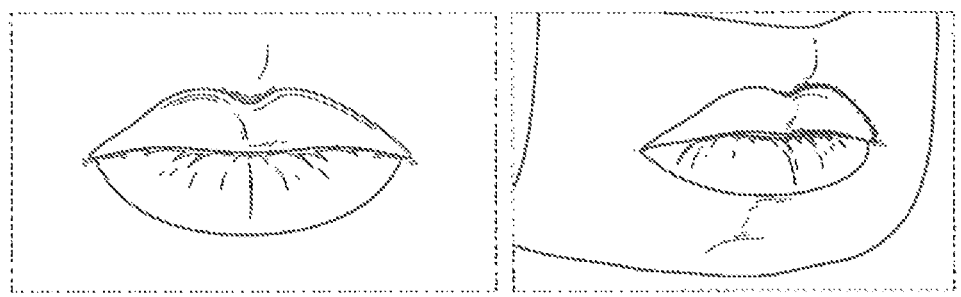
FIGS. 3A and 3B illustrate examples of the acquisition of the topography of the surface of the lips after application of a composition.

In the example of FIG. 3, a red lipstick has been applied, in a uniform coat, to at least part of the lips and to the skin around the lips of a user, before the 3D scan. This lipstick has advantageously been applied in such a way as to redefine the outline of the lips in the way chosen by the user. Because this lipstick exhibits a pronounced difference in color compared with the rest of the face, the outline of the region to which the composition is applied is readily recognized by the 3D scanner 31. The composition may be applied differently from a uniform coat, for example along a line defining the outline of the lips. FIG. 3(b) shows the 3D acquisition of the surface thus covered with the lipstick.

Figure 4:
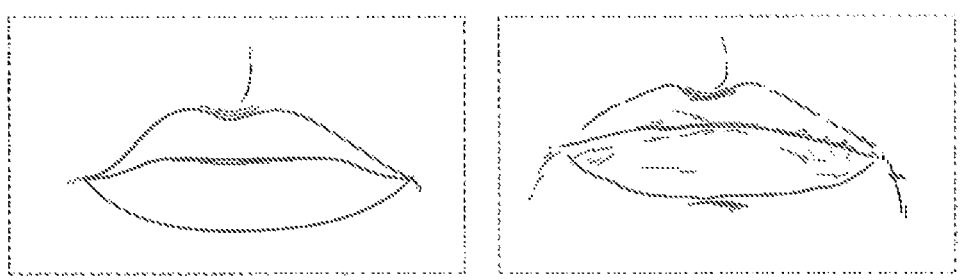
FIGS. 4A and 4B illustrate examples of the acquisition of the topography of the surface of the lips after application of a composition.

In the alternative form in FIG. 4, a silicone paste has been applied over a thickness of approximately 0.5 mm. That makes it possible, as seen in FIG. 4(b), for a 3D scanner unable to detect color, for example a Geomagic "Capture" 3D scanner, to make the acquisition of the outline of the region to which the composition has been applied.

In the alternative form of FIG. 5, a red or white lipstick has been used to look for the ideal shape of outline. In order for a 3D scanner unable to detect color to perform the acquisition, an adhesive filament, for example with a diameter equal to 0.5 mm, has been used along the outline defined by the lipstick. The make-up has then been removed from the lips in order to perform the 3D scan.

In the alternative form of FIG. 6, a white lipstick has been applied, in a uniform coat. Because the white lipstick exhibits a pronounced difference in color compared with the rest of the face, the outline of the region to which the composition is applied is readily recognized by the 3D scanner 31, as visible in FIGS. 6(a) and 6(b).

Figure 7:
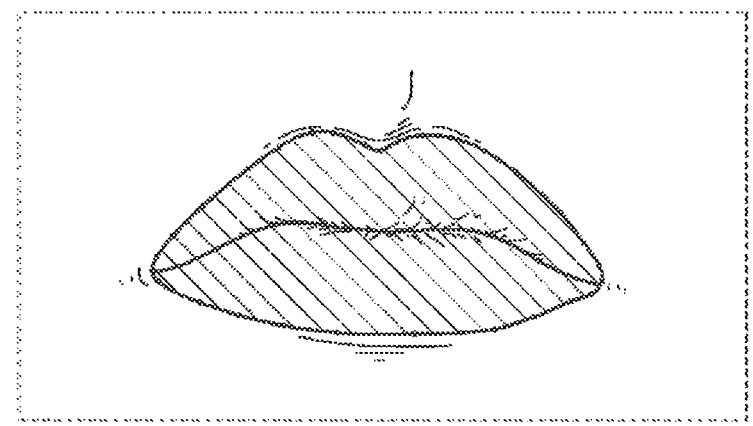
FIG. 7 illustrates the creation of a spline outlining curve.

An automatic outlining of the lips from an image thereof can be produced, it being possible to generate a "spline", having numerous control points, for example more than twenty or so, as illustrated in FIG. 7.

Figure 8:
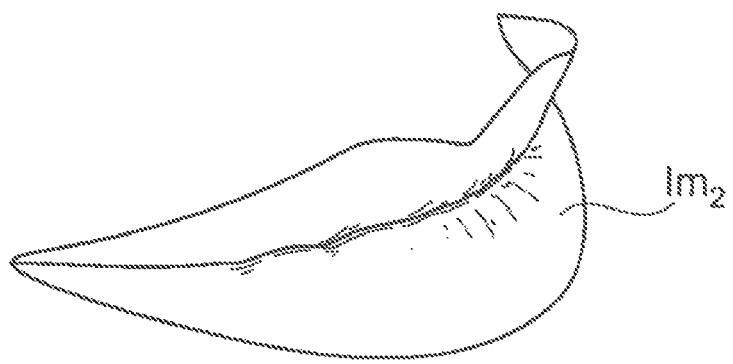
FIG. 8 depicts one example of the creation of a reworked surface.

It is possible to use image processing to isolate the regions from which to produce the applicator. Thus, FIG. 8 illustrates the captured region after the region outside the outlined outline has been eliminated, this corresponding to an image $Im_2$ of the application surface 2 of the applicator 1 that is in the process of being produced.

Figure 10:
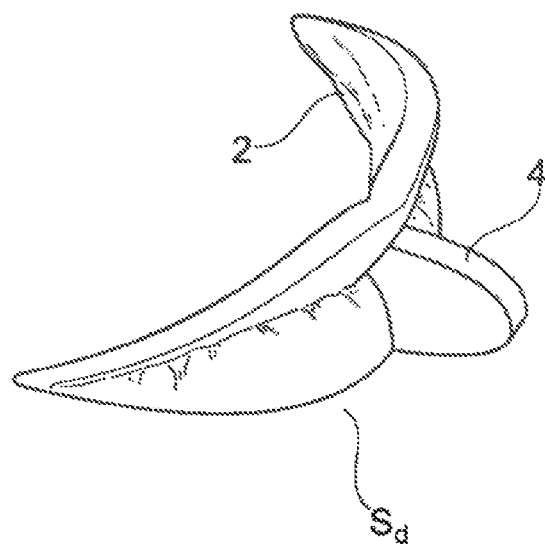
FIG. 10 illustrates the computer simulation of a personalized applicator.

FIG. 10 is a computer simulation of a personalized applicator according to the invention, after the creation of the volume visible in FIG. 9(b). In this example, a distinctive sign $S_d$ corresponding to the user's forename is inscribed on the applicator.

Figure 11:
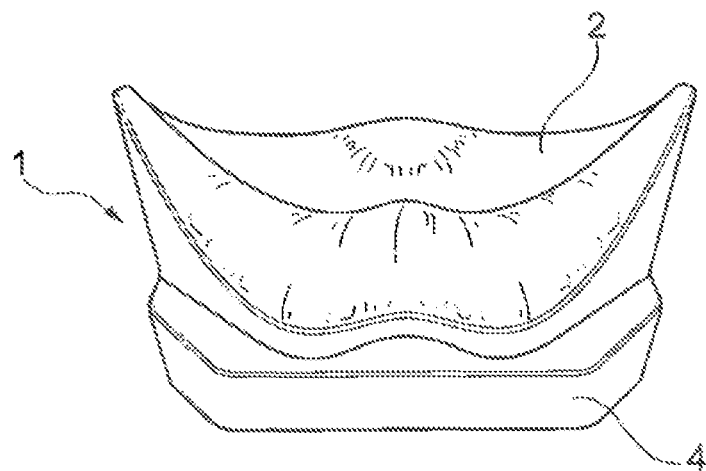
FIG. 11 illustrates an applicator produced according to the invention using machining.

In the example of FIG. 11, the personalized applicator 1 according to the invention, comprising a handle 4, has been manufactured by micro-machining, as described previously, on the basis of the surface defined in step 12. The user obtains her applicator for example between 5 and 15 minutes after the start of the operation and can use it immediately.

Figure 12:
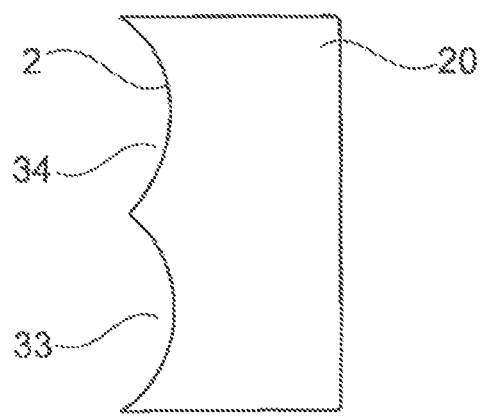
FIG. 12 depicts one example of a preform for using micro-machining to create an applicator according to the invention.

An example of a preform 20 used for creating the applicator 1 by micro-machining is depicted in FIG. 12. This preform has an upper cavity 34 corresponding to the upper lip, and a lower cavity 33 corresponding to the lower lip. This preform 20 can be chosen, notably automatically, from among many according to the shape that is to be obtained after machining. In this case, a computer program may indicate the preform best suited to the end result, for example which requires the least removal of material. The preform 20 can be machined by any technique that is compatible with the material used.

Figure 13:
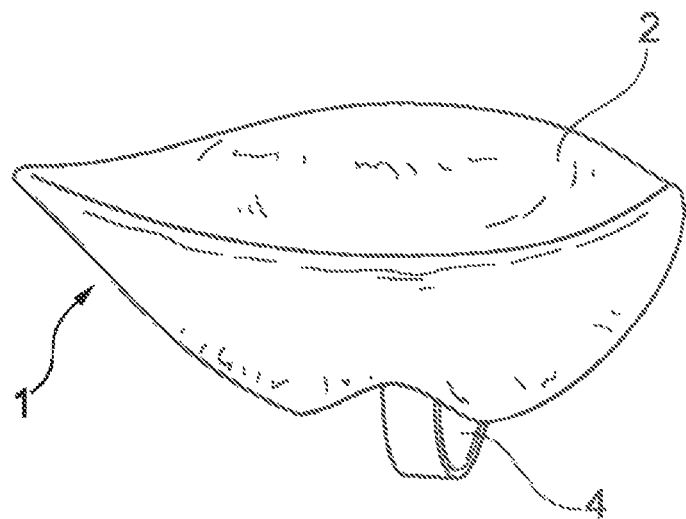
FIG. 13 depicts an alternative form of applicator produced by 3D printing.

In the alternative form of FIG. 13, the personalized applicator 1 has been manufactured by 3D printing on the basis of the surface defined in step 12, using for example a 3D printer 32 of the Ultimaker 3 type, loaded with an ABS filament. The user obtains her applicator approximately between 2 and 4 hours after the start of the operation and can use it, after first cleaning it.

Figures 14A, 14B:
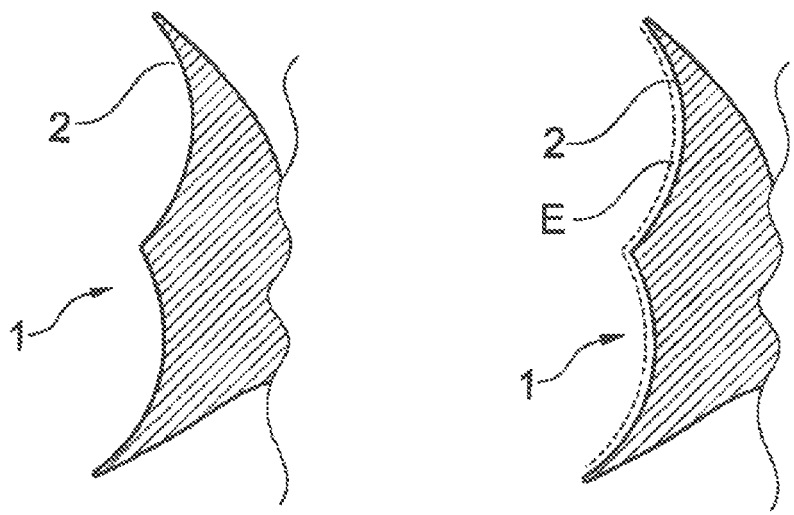
FIGS. 14A and 14B depict views in vertical and partial section, on a midplane, of alternative forms of applicator according to the invention.

FIG. 14A depicts the applicator of FIG. 13 viewed in vertical and partial section on a plane corresponding to the vertical midplane of the mouth. The application surface 2 which conforms to the shape of the lips is visible.

In the alternative form of FIG. 14B, a space E has been left between the application surface 2 and the scanned lips, indicated in dotted line. The reworked surface departs from the natural surface of the lips on the inside of the outline thereof, when the applicator is pressed onto the lips in the normal way. The applicator 1 can be used with a self-expanding composition which, as it expands, fills the space E left between the application surface 2 and the lips.

Figure 16:
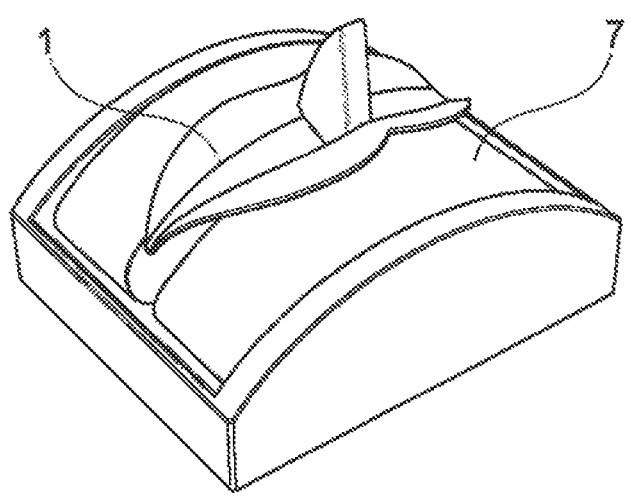
FIG. 16 depicts a pad impregnated with composition intended to load an applicator according to the invention.
Figure 17:
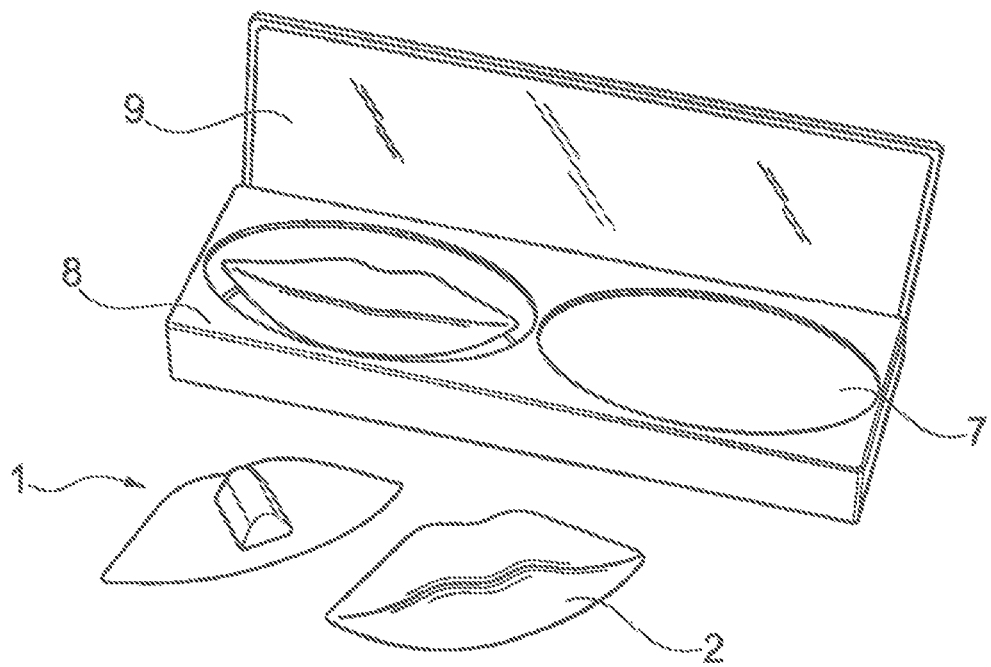
FIG. 17 depicts a box containing a personalized applicator according to the invention.

In the example of FIG. 13, the applicator 1 comprises a handle 4 on the back. It is intended to be brought into contact with a domed pad impregnated with composition, for example made of foam, as visible in FIG. 16, which readily adapts to the shape of the applicator. In the alternative form of FIG. 17, the personalized applicator 1 according to the invention and a pad 7 impregnated with composition are offered in a box 8, for example including a mirror 9.

In an alternative form which has not been illustrated, the applicator 1 is heated and laden with composition by being brought into contact with a compact of composition.

Figure 15:
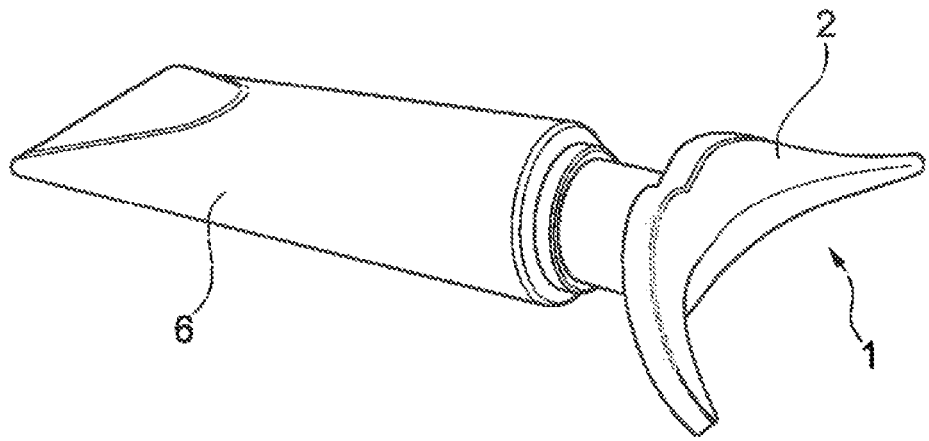
FIG. 15 depicts an alternative form of applicator comprising a product reservoir.

In the alternative form of FIG. 15, the applicator 1 has been produced in such a way that it can be mounted on a reservoir 6 containing the make-up product. The reservoir 6 is, for example, a flexible tube. However, the invention is not limited to one particular type of applicator or of reservoir or pad.

Figure 18:
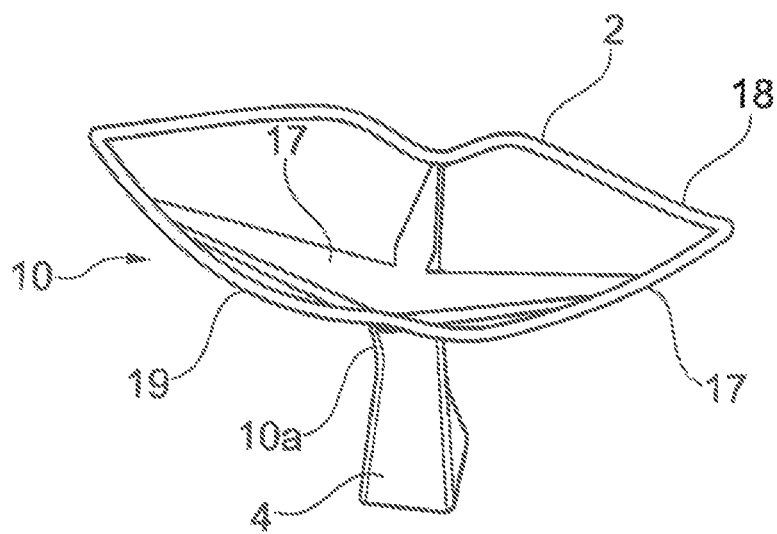
FIGS. 18 and 19 depict alternative forms of applicator according to the invention, in which the application surface is configured to apply the composition only to their periphery, so as to outline the lips with make-up only.
Figure 20A:
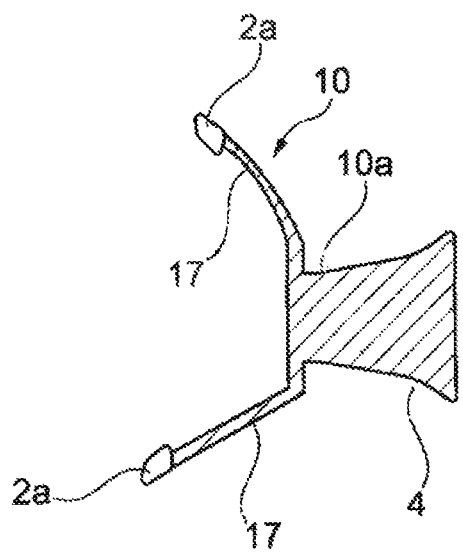
FIGS. 20A, 20B, 20C, and 20D depict views in vertical and partial section, on a midplane, of alternative forms of applicator according to the invention, for outlining the lips with make-up only.

In the alternative form illustrated in FIGS. 18 and 20A, a personalized applicator 10 according to the invention, manufactured as described hereinabove, has an application surface 2 configured for applying the composition only to the periphery of the lips so as to make up their outline only. In the example concerned, the application surface 2 is defined by a filamentary part of the applicator 10. In this example, the applicator 10 comprises a central part 10a, extended by the handle 4, and four arms 17 extending from said central part 10a and at their ends and in their middle supporting the upper and lower parts 18, 19 of the applicator 10 that form the outline of the upper and lower lips respectively. The upper and lower parts 18, 19 meet at their ends.

Figure 19:
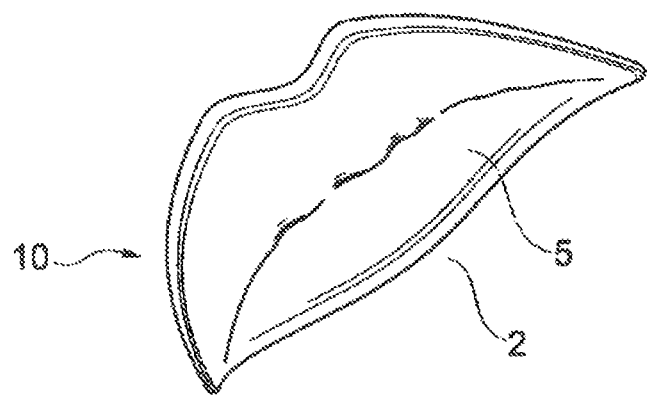
Figure 20B:
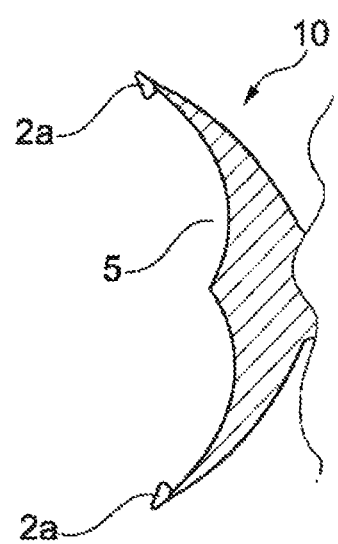

In the alternative form of FIGS. 19 and 20B, the application surface 2 is defined by a hollowed part 5 of the applicator 10.

Figure 20C:
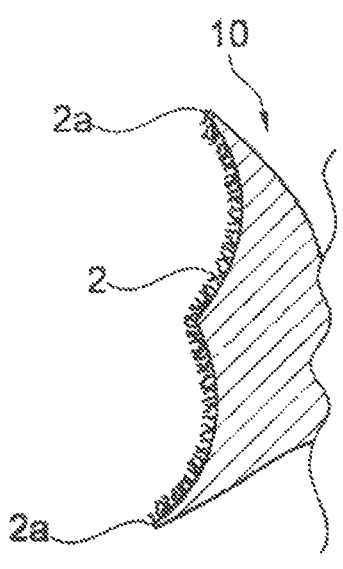

In the alternative form of FIG. 20C, the application surface 2 is solid, the application surface 2, with the exception of the peripheral part 2a thereof, is coated in flock.

Figure 20D:
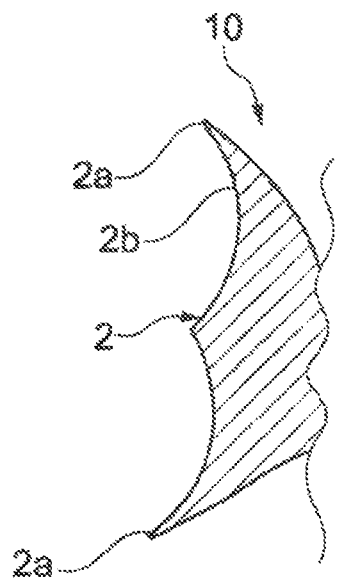

In the alternative form of FIG. 20D, the applicator 10 is made of two materials: the peripheral part 2a of the solid application surface 2, which is intended for making up the outline of the lips, is made from a material capable of becoming laden with composition, the inside 2b of the application surface 2 being made from a different material less, or even not at all, able to become laden with composition.

The outlines of these applicators 10 may be produced to follow the exact shape of the mouth or to follow a redefined shape, as explained hereinabove.

Figure 21A:
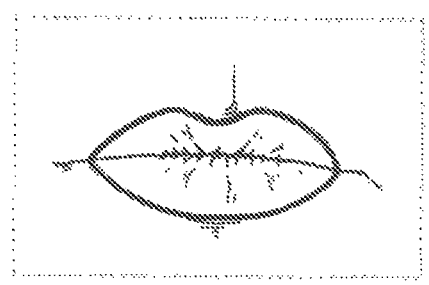
FIGS. 21A and 21B show examples of results of the application of make-up to the outline of the lips using applicators according to the invention which outline the lips with make-up only.
Figure 21B:
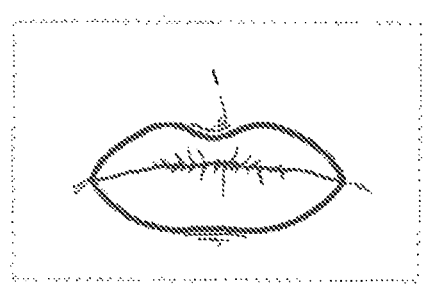
Figure 24A:
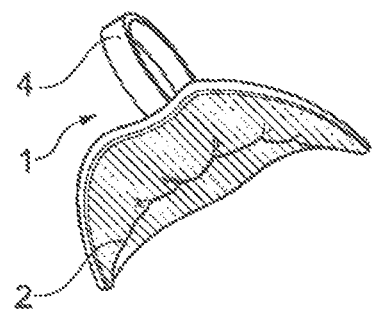
Figure 24B:
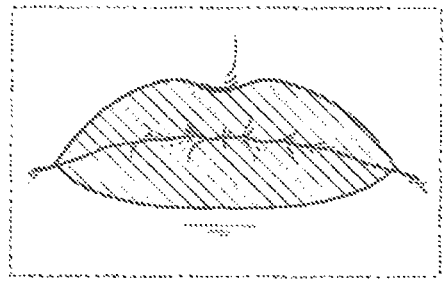
Figure 24C:
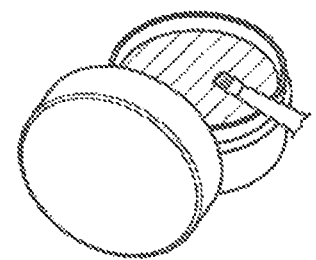
Figure 24D:
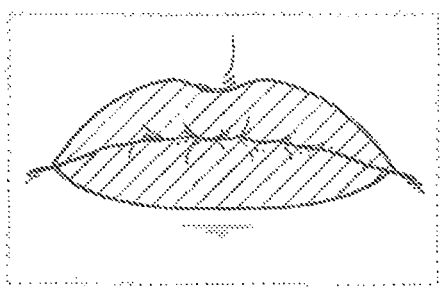
Figure 25A:
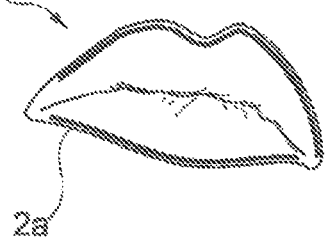
FIGS. 25A, 25B, 25C, and 25D illustrate a lip make-up achieved with an applicator according to the invention and an adhesive composition.
Figure 25B:
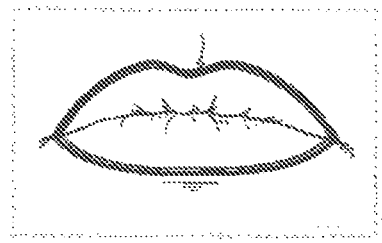
Figure 25C:
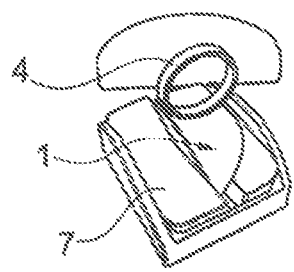
Figure 25D:
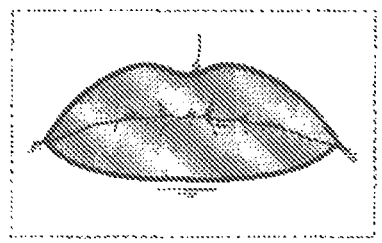
Figure 26A:
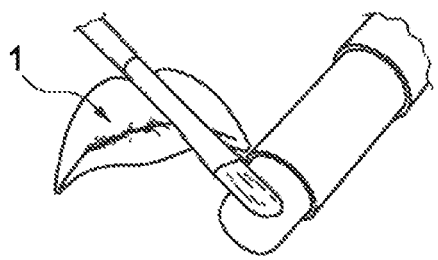
FIGS. 26A, 26B, 26C, and 26D illustrate a lip make-up achieved with an applicator according to the invention and an adhesive composition.
Figure 26B:
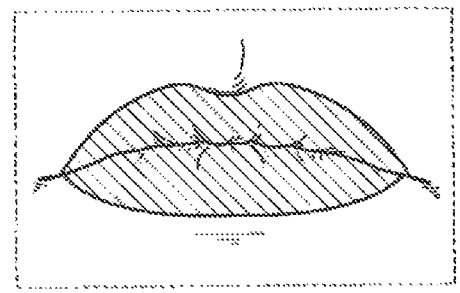
Figure 26C:
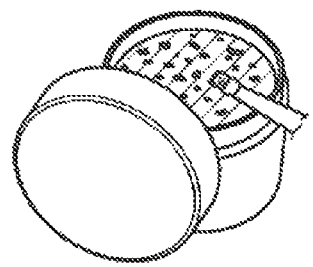
Figure 26D:
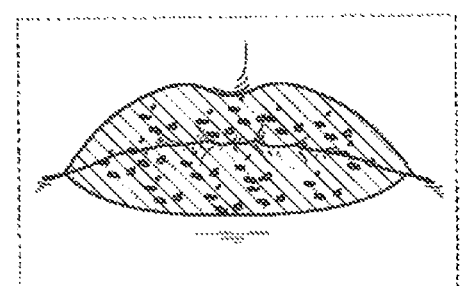
Figure 27A:
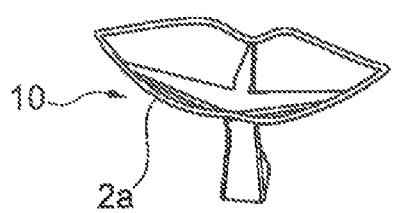
FIGS. 27A, 27B, 27C, and 27D illustrate a lip make-up achieved with an applicator according to the invention and an adhesive composition.
Figure 27B:
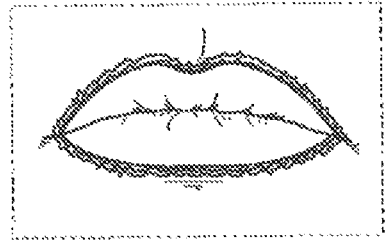
Figure 27C:
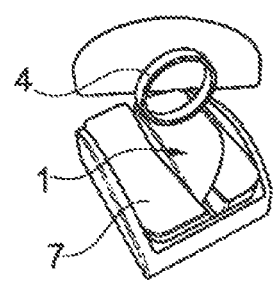
Figure 27D:
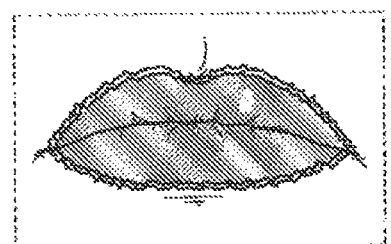

FIG. 21(a) shows a result of the use of a filamentary personalized applicator 10 for making up the outline of the lips. FIG. 21(b) shows a result of the use of a hollowed personalized applicator 10. In these two examples, the user has outlined the outline of her lips using the applicator 10 by loading the application surface 2 using a pad impregnated with composition and pressing it against her lips. The outlines are very clean and very attractive. In an alternative form which is not illustrated, the space inside the outline is filled with a cosmetic composition of the same color as or of a different color than the one used for the outline. The applicator used for doing this is advantageously a personalized applicator 1 according to the invention, or a stick of lipstick according to the prior art.

A comparison between the lip make-up results obtained with a lipstick applicator of the prior art, for example of the stick of lipstick type, and with a personalized applicator 1 according to the invention, is depicted in FIG. 22. The make-up obtained with the personalized applicator 1, visible on the right, is of high quality, the outlines are very clean and very attractive. The lips appear to have been remodeled and appear more plump. Subtle changes in lip outline, at millimeter scale, are enough to make a very pronounced change to the look of the lips and improve the overall harmony of the face.

In the example of FIG. 23, a first composition, a glucose syrup, for example made by Scrap Cooking, has been applied to the application surface 2 of an applicator 1 according to the invention, the applicator 1 then being used to apply to the lips of a user. A second composition, nonpareil sugar balls, Silikomart Mini Wonder Pearls made by Wonder Cakes in this example, are applied with a brush to the lips thus coated with the first composition.

In the example of FIG. 24, a glucose syrup is once again applied to the user's lips using an applicator 1 according to the invention. A second composition, an edible iridescent blue powder made by Scrap Cooking in this example, is applied with a brush to the lips thus coated with the first composition.

In the example of FIG. 25, a first composition, a matte liquid lipstick in a first color, is applied exclusively to the outline of the lips using an applicator 10 according to the invention, then a second composition, a matte liquid lipstick of a second color, different than the first, lighter in the example considered, is applied to the entirety of the lips using an applicator 1 according to the invention laden with composition by a pad 7 impregnated with said second composition.

In the example of FIG. 26, a first composition, a solid greasy red lipstick, has been applied by brush to the application surface 2 of an applicator 1 according to the invention, the applicator 1 then being used to apply to the lips of a user. Edible gold glitter, made by Scrap Cooking in this example, is applied with a brush to the lips thus coated with the first composition.

In the example of FIG. 27, an adhesive composition, such as Pros-Aid Adhesive by ADM Tronic, is applied to an applicator 10 according to the invention and is then applied exclusively to the outline of the lips. Edible gold leaf is then applied with a brush to the outline thus coated with the adhesive composition, as visible in FIG. 27(b). A second composition, a matte liquid lipstick in the example considered, is applied to the entirety of the lips using an applicator 1 according to the invention laden with composition by a pad 7 impregnated with said second composition.

Personalized applicators according to the invention allow uniform results to be obtained very quickly after just a few attempts.

Various examples of implementations methods for manufacturing a personalized applicator according to the invention will now be described.

EXAMPLE 1

Figure 28:
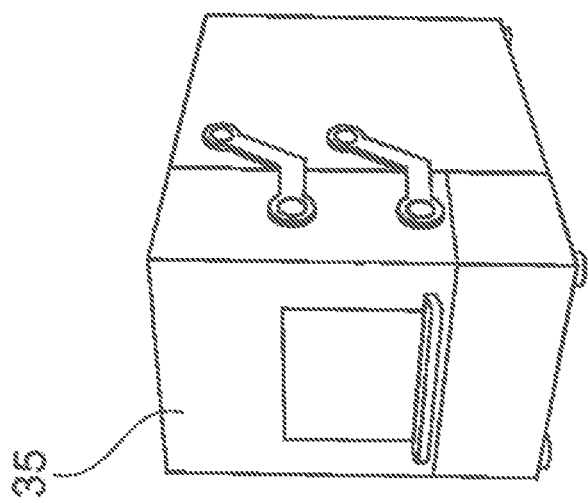
FIG. 28 illustrates one example of the sequence of steps in a method for manufacturing a personalized applicator according to the invention.
Figure 28:
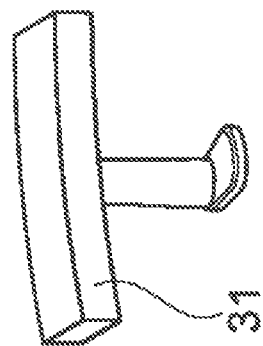
Figure 28:
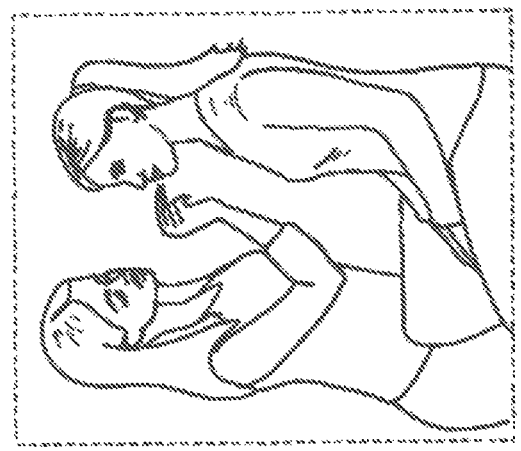

In a first example illustrated in FIG. 28, a user desirous of a personalized applicator goes to a sales outlet or to an institute where there is a make-up artist who guides her through the creation of her applicator. The make-up artist applies a red lipstick to the user's lips, looking for the ideal shape of the lip outline, and defines the lip outline that best suits the individual, for example in terms of the overall harmony of the face, making successive small adjustments until she is satisfied. A 3D scan of the topography of the surface of the lips thus covered in composition is then made using a color 3D scanner 31. A 3D surface and the volume of the applicator are generated from the result of the scan, with the outline defined by the make-up artist, as described hereinabove, and a micro-machining tool 35 is used to manufacture the applicator 1, an example of which is depicted in FIG. 11.

EXAMPLE 2

This example is identical to the preceding example except that the make-up artist operates at a different location than the location at which the 3D scan will be performed, the make-up artist having, for example visited the user at home, or the user having visited the make-up artist's salon. The user then goes to a sales outlet where the 3D acquisition and the manufacture of the applicator are performed by an operator.

EXAMPLE 3

In this example, after the make-up artist has found the ideal shape for the outline of the lips by applying a composition and taking a 3D scan of the topography, the user leaves the location where that has been performed, with her lips thus made-up, and takes advantage of this to gather opinions from those around her. She then sends the make-up artist the order either to make the applicator, or not do so. In the affirmative, the make-up artist sends the corresponding 3D file to the chosen location and an operator creates the applicator. Alternatively, the user may rely upon the opinion of those around her to get the make-up artist to make changes.

EXAMPLE 4

In this example, the step of determining the ideal shape is performed by establishing a remote connection with a third party guiding the individual, for example on her computer. No composition is applied to the lips beforehand, and the search for the ideal outline is performed using software on the 3D scan of the lips. The user may be given the option to choose between several make-up results. The reworked surface is generated from this choice, and the applicator is then created using 3D printing. The user may choose the location at which the applicator is created and go there to collect it. It may also be sent to her at home.

EXAMPLE 5

In this example, an electronic assistant guides the user on her smart phone, to create the ideal outline. The individual applies a composition to her lips before the 3D scan. The applicator 10 is produced by micro-machining with a filamentary structure and has an application surface 2 configured for applying the composition to the periphery of the lips only, so as to make-up their outline only, as visible in FIG. 18.

Of course, the invention is not limited to the exemplary embodiments that have just been described.

The personalized applicators manufactured according to the invention may be configured to apply a cosmetic composition to an area of keratinous materials other than the lips, for example the eyelids.

The invention claimed is:

1. A method for manufacturing a personalized applicator for applying a product to keratinous materials, comprising an application surface, the method comprising the following steps:

a) applying to a surface of the keratinous materials of an individual a composition that modifies of an appearance of said keratinous materials,
   b) performing an optical acquisition of the topography of the surface thus covered and of at least one image providing information as to the location of the composition, and
   c) from this acquisition creating the applicator or a mold intended for the manufacture thereof.

2. The method as claimed in claim 1, the surface to which the composition is applied extending over at least part of the lips.

3. The method as claimed in claim 2, the surface to which the composition is applied extending over at least part of the skin around the lips.

4. The method as claimed in claim 1, the composition being applied in such a way as to redefine the outline of the lips.

5. The method as claimed in claim 4, the composition over spilling onto the skin at least at one point.

6. The method as claimed in claim 4, the composition being applied to at least one place that is set back from the natural outline of the lips.

7. The method as claimed in claim 1, the composition being applied in such a way as to redefine the Cupid's bow.

8. The method as claimed in claim 1, the composition being applied in such a way as to modify the height of the lips and/or the width of the lips and/or correct a symmetry.

9. The method as claimed in claim 1, the outline of the application surface of the applicator diverging from the natural outline of the lips.

10. The method as claimed in claim 1, the composition being a lipstick.

11. The method as claimed in claim 1, the composition being a white lipstick.

12. The method as claimed in claim 1, the composition being applied as a uniform coat.

13. The method as claimed in claim 1, the composition being applied along a line defining a zone.

14. The method as claimed in claim 1, the keratinous materials being made up according to a result validated by the individual and the composition then being applied to the same outline as the one just validated, so that said acquisition can be done.

15. The method as claimed in claim 1, the make-up result obtained after application of the composition being validated by the individual before proceeding with the optical acquisition of the topography of the surface.

16. The method as claimed in claim 1, the topography being obtained by a 3D scan of the surface covered with composition.

17. The method as claimed in claim 1, involving generating a file that can be read by a CNC machine or a 3D printer.

18. The method as claimed in claim 16, comprising a step involving generating a reworked 3D surface from the data derived from the optical acquisition of the topography of the surface.

19. The method as claimed in claim 1, involving automatically outlining the region covered with composition by using image processing.

20. The method as claimed in claim 1, involving manually identifying points in the image of the region covered with composition and automatically determining, from these points, an outline used to create the applicator or the mold.

21. The method as claimed in claim 1, involving displaying on a screen at least one model of an application, the composition being applied according to this model.

22. The method as claimed in claim 21, involving establishing a remote connection to a third party providing a model to propose according to the physiognomy of the individual.

23. The method as claimed in claim 21, involving establishing a remote connection with a third party who guides the individual through the application of the composition.

24. A method of applying make-up using an applicator obtained by implementing the method as claimed in claim 1, involving bringing the applicator into contact with the keratinous materials of said individual and transferring a make-up product onto said materials.

25. The method of applying make-up as claimed in claim 24, implemented for applying make-up to the lips, said keratinous materials comprising at least part of the lips and, if appropriate, of an adjacent area of skin.

26. The method as claimed in claim 1, wherein the product is a make-up product.

27. The method as claimed in claim 13, wherein said zone is the outline of the lips.

28. The method as claimed in claim 14, the make-up then being removed.

29. The method as claimed in claim 16, wherein the topography is obtained by projecting structured light onto said surface.

30. The method as claimed in claim 18, wherein said step involves generating a reworked 3D surface using image processing software.

31. The method as claimed in claim 21, involving selecting a model.

* * * * *